United States Patent
Stella et al.

(10) Patent No.: US 10,028,977 B2
(45) Date of Patent: *Jul. 24, 2018

(54) EFFERVESCENT DOSAGE FORM

(71) Applicant: The Procter & Gamble Company, Cincinnati, OH (US)

(72) Inventors: Mark Edward Stella, Cincinnati, OH (US); John Richard Entwisle, Mason, OH (US); Jason William Newlon, Lebanon, OH (US); Christine Louis Naykki, Deerfield Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/482,937

(22) Filed: Apr. 10, 2017

(65) Prior Publication Data

US 2017/0209487 A1    Jul. 27, 2017

Related U.S. Application Data

(63) Continuation of application No. 14/715,628, filed on May 19, 2015, now Pat. No. 9,649,274, which is a continuation of application No. 13/915,636, filed on Jun. 12, 2013, now abandoned.

(60) Provisional application No. 61/658,430, filed on Jun. 12, 2012.

(51) Int. Cl.
| | |
|---|---|
| *A61K 31/695* | (2006.01) |
| *A61K 33/10* | (2006.01) |
| *A61K 9/46* | (2006.01) |
| *A61K 9/00* | (2006.01) |
| *A61K 9/20* | (2006.01) |

(52) U.S. Cl.
CPC ............ *A61K 33/10* (2013.01); *A61K 9/0007* (2013.01); *A61K 9/0056* (2013.01); *A61K 9/2009* (2013.01); *A61K 9/2013* (2013.01); *A61K 9/2018* (2013.01); *A61K 9/2036* (2013.01); *A61K 9/2059* (2013.01)

(58) Field of Classification Search
None
See application file for complete search history.

(56) References Cited

U.S. PATENT DOCUMENTS

| | | | |
|---|---|---|---|
| 4,083,951 A | 7/1978 | Goudie et al. | |
| 4,198,390 A | 4/1980 | Rider | |
| 4,396,604 A | 8/1983 | Mitra | |
| 4,650,669 A | 3/1987 | Alexander et al. | |
| 4,678,661 A | 7/1987 | Gergely et al. | |
| 5,073,384 A | 12/1991 | Valentine et al. | |
| 5,225,197 A * | 7/1993 | Bolt | A61K 9/0056 424/440 |
| 5,312,626 A | 5/1994 | Gergely et al. | |
| 5,330,760 A | 7/1994 | Walton | |
| 5,458,886 A | 10/1995 | Briquet | |
| 5,543,153 A * | 8/1996 | Walton | A61K 9/0007 424/441 |
| 5,807,577 A | 9/1998 | Ouali | |
| 5,869,095 A | 2/1999 | Gergely et al. | |
| 5,888,544 A | 3/1999 | Gergely et al. | |
| 6,245,353 B1 | 6/2001 | Tritthart et al. | |
| 6,489,346 B1 | 3/2002 | Phillips | |
| 6,544,557 B2 | 4/2003 | Selim | |
| 6,579,535 B2 | 6/2003 | Valentine et al. | |
| 6,589,507 B1 | 7/2003 | Bauer | |
| 6,589,555 B2 | 7/2003 | Pandya | |
| 7,638,143 B2 | 12/2009 | Piene et al. | |
| 8,007,752 B2 | 8/2011 | Piene et al. | |
| 2003/0235613 A1 | 12/2003 | First et al. | |
| 2004/0223921 A1 | 11/2004 | Rau et al. | |
| 2005/0074489 A1 | 4/2005 | Gonzales et al. | |
| 2005/0263430 A1 | 12/2005 | Istituto et al. | |
| 2006/0057078 A1 | 3/2006 | Rau et al. | |
| 2006/0078508 A1 | 4/2006 | Gebreslassie et al. | |
| 2009/0004248 A1 | 1/2009 | Bunick et al. | |
| 2011/0014132 A1 | 1/2011 | Liu | |

FOREIGN PATENT DOCUMENTS

| | | |
|---|---|---|
| CN | 102232967 A | 11/2011 |
| EP | 396335 A1 | 7/1990 |
| EP | 788791 | 8/1997 |
| EP | 2189154 A1 | 5/2010 |
| GB | 2148117 A | 5/1985 |
| WO | WO 94/00107 A1 | 1/1994 |
| WO | WO 2011113965 | 9/2011 |

OTHER PUBLICATIONS

PCT International Search Report dated Oct. 17, 2013—4 pages.
Colas, Andre et al., Silicones in Pharmaceutical Applications, pp. 1-4, 2006.
All office actions for U.S. Appl. No. 13/915,636, filed Jun. 12, 2013.
All office actions for U.S. Appl. No. 14/715,628, filed May 19, 2015.

* cited by examiner

*Primary Examiner* — Craig D Ricci
(74) *Attorney, Agent, or Firm* — Amanda Herman

(57) ABSTRACT

An effervescent chewable dosage form that comprises a pH neutralization agent, an acid, and an effervescent agent. The chewable dosage form can also further comprise simethicone, a sweetener, and a lubricant. The pH neutralization agent can be calcium carbonate, the acid can be citric acid and the effervescent agent can be sodium bicarbonate.

15 Claims, 2 Drawing Sheets

| Time in Minutes | pH |
|---|---|
| 0.0 | 5.73 |
| 0.5 | 5.53 |
| 1.0 | 5.53 |
| 2.0 | 4.76 |
| 5.0 | 4.91 |
| 10.0 | 5.42 |
| 15.0 | 5.73 |
| 30.0 | 6.20 |
| 60.0 | 6.34 |
| 75.0 | 6.48 |
| 90.0 | 6.53 |
| 120.0 | 6.56 |
| 180.0 | 6.68 |
| 210.0 | 6.73 |
| 300.0 | 6.96 |
| 4320.0 | 8.50 |

EFFERVESCENT DOSAGE FORM

FIELD OF THE INVENTION

The invention is generally directed to chewable effervescent dosages, and more particularly to effervescent antacids that provide relief of heartburn, acid indigestion, sour stomach and/or gas.

BACKGROUND OF THE INVENTION

Many people experience gastrointestinal symptoms such as heartburn, and indigestion.

Consumers want fast relief from their gastrointestinal symptoms as well as a pleasant sensory experience. There are many over the counter products that are available to treat gastrointestinal symptoms, however they do not provide the speed and sensory experience that the consumer desires. Some drugs, such as proton pump inhibitors, take at least several hours for the consumer to experience relief and can negatively interact with many commonly prescribed medications, such as clopidogrel. Antacids generally provide relief faster than proton pump inhibitors, but have some unpleasant sensory experiences. Consumers often complain that chewable antacids have a chalky taste, an unpleasant lingering aftertaste, toothpacking, and a gritty texture. Consumers who take liquid antacids similarly complain about an unpleasant taste and aftertaste as well as the inconvenience of taking a liquid medication, especially when they are not at home.

Many consumers like an effervescent product because the effervescence can help reduce pressure in their gastrointestinal tract and consumers believe that the effervescence signals that the product is working. However, consumers find current effervescent products unsatisfactory. Many effervescent products have to be dissolved in water which makes them inconvenient to take, especially when the consumer is not at home. Furthermore, consumers do not enjoy the sensory experience as they complain that the effervescence is too strong and the taste is too salty and/or sour.

As such, there remains a need for a convenient effervescent product that quickly relieves heartburn and indigestion, and releases pressure while providing a pleasant sensory experience.

SUMMARY OF THE INVENTION

An effervescent chewable dosage form comprising: from 26% to 40% of a pH neutralization agent; from 3% to 10% of an acid; and from 3% to 10% of an effervescent agent.

An effervescent chewable dosage form comprising: from 28% to 34% calcium carbonate; from 4% to 6% citric acid; from 5% to 7% sodium bicarbonate; and from 35% to 50% sweetener.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

Figure 1:
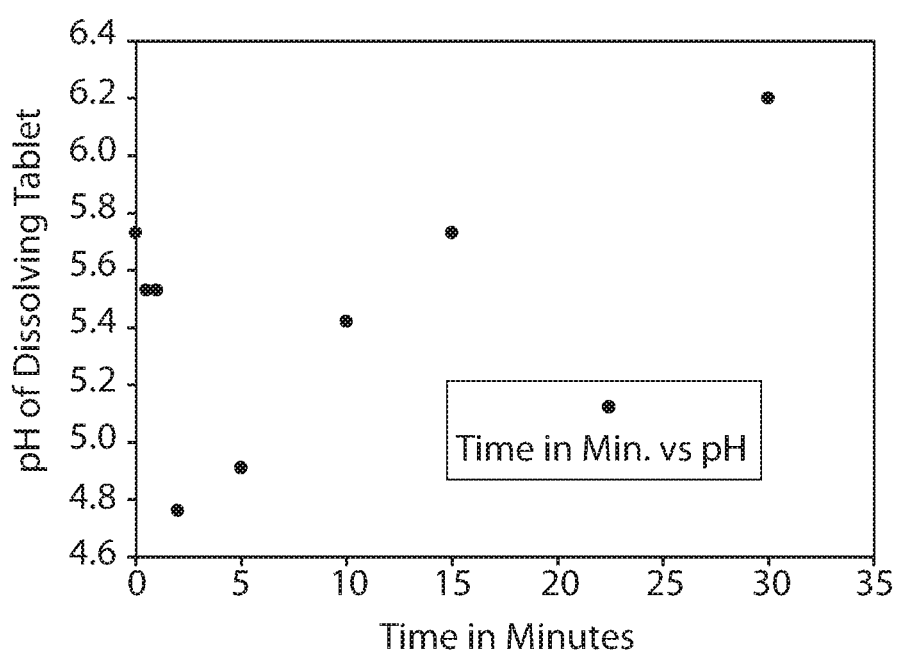
FIG. 1 is a pH Profile of Effervescent Chewable Tablet over 35 Minutes.

The present invention relates to chewable effervescent dosage forms that can be orally administered without water. Such dosage forms can provide fast relief of heartburn, indigestion, and release pressure in the upper gastrointestinal tract while providing a pleasant sensory experience. The effervescence can also provide a signal to the consumer that the product is working. When the consumer places the dosage form, for example a chewable tablet, into her oral cavity the dosage form effervesces. As the consumer chews, the dosage form can easily fracture. Some portions of the dosage form can dissolve in the oral cavity, providing the sensory experience, while other portions can dissolve in the stomach providing the gastrointestinal relief. The dosage form can be easily swallowed and shortly after the dosage form has been swallowed, the consumer experiences little mouthcoating, aftertaste, and toothpacking while the effervescence helps relieve pressure and provides an indication of fast relief.

The sensory experience of this product is affected by the composition and increasing or decreasing the amount of any one component, in particular the pH neutralization agent, the acid, and/or the effervescent agent, can significantly change the sensory experience. For instance, if too much acid is incorporated into the dosage forms, the dosage form can taste too sour, it can foam too much, and the effervescence can be too strong. However, if there is not enough acid in the dosage form, then the effervescence can be too weak and the composition can taste too chalky. Likewise, if the effervescence is too strong, it can irritate the consumer's mouth and gastrointestinal tract and can cause a burning sensation in the throat, which may already be irritated if the user has heartburn.

As used herein "gastrointestinal symptoms" can include any symptom in the upper or lower digestive tract. Non-limiting examples of gastrointestinal symptoms can include sour stomach, diarrhea, constipation, upset stomach, vomiting, cramps, gas, bloating, stomach ache, heartburn, flatulence, and combinations thereof. In one example, the dosage form can be used to treat heartburn. In one example, the dosage form can be used to treat more than one digestive symptom, for example heartburn and gas.

As used herein, "effervescent" or "effervescence" refers to emitting small bubbles of gas continuously produced for a period of time.

As used herein, the term "foam", "foamy", or "foaming" refers to a mass of frothy bubbles of air or gas in a matrix of liquid film that expands in size over time.

As used herein, the term "friability" refers to the force with which a portion of the dosage form breaks.

As used herein, "grittiness", "gritty", or "grit" refers to a texture that is similar to fine, rough, granules. In one example, a dosage form could be considered gritty if, as it is chewed and/or dissolved in the oral cavity, the texture resembles granules of sand.

As used herein, "hardness" refers to the resistance of a surface to penetration or indentation.

As used herein, the term "indicia" means identifying marks or indications that provide information to the consumer. Non-limiting examples of indicia can include branding, words, phrases, letters, characters, brand names, company names, company logos or symbols, logos, icons, designs, designer names, insignias, shapes, alpha-numeric symbols, pictures, drawings, illustrations, photographs, computer-produced images, colors, sounds, textures, shapes, letters, numbers, and combinations thereof.

As used herein, the term "mouthcoating" refers to the amount of dosage form left on the oral cavity surfaces after the dosage form is swallowed.

As used herein, the term "relief" or "relieving" refers to alleviating one or more gastrointestinal symptoms in a human.

As used herein, the term "toothpacking" refers to the amount of the dosage form left on or stuck in or between the teeth after swallowing the dosage form.

As used herein, the term "treat" or "treating" includes preventing, alleviating, ameliorating, inhibiting, or mitigating one or more gastrointestinal symptoms in a human.

As used herein, the articles "a" and "an" is understood to mean one or more of the material that is claimed or described, for example, "a dosage form" or "an acid".

All weights, measurements and concentrations herein are measured at 23 degrees Celsius (° C.) and 50% relative humidity, unless otherwise specified.

All percentages, parts and ratios as used herein are by weight of the total dosage form, unless otherwise specified. All such weights as they pertain to listed ingredients are based on the active level and, therefore do not include solvents or by-products that may be included in commercially available materials, unless otherwise specified.

The article, process and methods of the present invention can comprise, consist of, or consist essentially of, the essential elements and limitations of the invention described herein, as well as any additional or optional ingredients, components, or limitations described herein or otherwise useful in personal health care articles intended for use or consumption by humans.

The dosage form can be effervescent, such as for example, a chewable effervescent dosage form. The effervescence can provide a consistent, gentle, steady release of small bubbles, similar to champagne. Effervescence can improve the consumer experience by helping reduce the chalky taste, toothpacking, and by helping to provide the impression of reduced pressure in the upper gastrointestinal tract. The active ingredients, such as the pH reducing agent and the gas reducer, can also help provide soothing relief of heartburn, acid indigestion, sour stomach and/or gas, while the effervescence provides tactile, visual feedback that the product is working.

Determining the correct amount of effervescence can be important to the consumer's experience when ingesting the dosage form. The correct amount of effervescence can be soothing to the consumer as well as help to relieve pressure in the upper gastrointestinal tract. If the effervescence is too strong the consumer can find it irritating, effervescence that is too strong can tickle the consumer's nose, oral cavity, and throat and cause further irritation. If the effervescence is too weak then the consumer may not experience the pressure relief in the upper gastrointestinal tract and the dosage form can have a chalkier taste.

In one example, the dosage form can have little foam. In another example, the dosage form can have a foam profile that is quickly generated and then quickly dissipates. In another example, the dosage form can have foam that is light and airy and that can quickly dissipate and/or can be easily swallowed. If the foam is too dense, too expansive, and/or does not dissipate quickly enough it can be difficult to swallow, which is particularly uncomfortable for consumers with gastrointestinal upset. Additionally, swallowing too much foam can make consumers feel more bloated, which can exacerbate an already bloated gastrointestinal tract. In one example, the dosage form as described herein does not form a thick foam. Instead, the foam can quickly dissipate into a thin, watery liquid that is easy to swallow.

Taste is an important attribute, especially in a chewable tablet. Consumers often complain that effervescent products have a salty or sour taste. If the product does not have a flavor that consumers like, then consumers will hesitate to ingest the product. Having a good taste improves consumer compliance because they do not mind or even enjoy taking the medication. In one example, the dosage form has a cherry flavor and when combined with the acid in the composition it resembles sour cherry. It has been found that for effervescent dosage forms many consumers prefer a flavor that is both sour and sweet. The flavor plus the effervescent can provide a delightful sensory experience, which can ultimately improve consumer compliance.

Antacid dosage forms can often have a chalky taste, as well as a chalky feeling on the consumer's hands and mouth. This chalkiness can be caused by the calcium carbonate active. The dosage forms in the present invention can have a less chalky taste and/or feel than other antacids, even though they can contain the same amount of calcium carbonate. While not wishing to be bound by theory, it is believed that the effervescent dosage form can help reduce the perception of chalkiness by providing a distracting sensory experience of effervescence. Furthermore, in one example, the combination of pH reducing agent, acid, effervescent agent, as well as flavor can further reduce the perception of chalkiness.

As the dosage form of the present invention dissolves, it can feel smoother than other antacid dosage forms. The dosage form as described herein can quickly dissipate into a thin, watery liquid. While not wishing to be bound by theory, it is believed that the effervescence can help reduce the perception of grittiness by helping to quickly break up the dosage form.

A dosage form has a certain hardness and friability. The dosage forms can be hard enough to withstand the rigors of handling and transportation experienced in the manufacturing plant, in the drug distribution system, and in the field in the hands of the consumer. If the dosage form is too soft it can fall apart or get crushed into a powder or pieces before the consumer can consume it. Conversely, if the dosage form is too hard it can be difficult to chew and it can produce more sound when it is chewed. Furthermore, hardness is also an important characteristic to provide the correct mouthfeel for a chewable product, if the product is too soft or too hard it may not have the correct texture when chewed.

The tablet breaking force is a measure of hardness and can be measured using USP Test Method 1217 using a Vankel Benchsaver VK200 Tablet Hardness Tester. In one example, the dosage form has a tablet breaking force from 2 kiloponds (kp) to 14 kp, in another example from 3 kp to 12 kp, in another example 4 kp to 8.5 kp, and in another example 5 kp to 7 kp.

Friability can be measured using USP Test Method 1216. The dosage forms can have lower friability than other antacids which means that the solid dosage form can be reduced to smaller pieces with less effort, which can ultimately lead to a faster dissolution of the dosage form.

Furthermore, the dosage form can have little sound as it effervesces and as it is chewed. Consumers can be concerned with attracting attention, especially when they are feeling sick, by consuming a noisy dosage form that pops and fizzes as it effervesces and/or loud crunching sounds as it is chewed.

Furthermore, a problem with many oral dosage forms, in particular antacids, is toothpacking, which can occur for an extended period of time. Consumers generally dislike toothpacking because it can be irritating, uncomfortable, and removing the particles can be embarrassing. Furthermore, if the product remains in the teeth then consumers can continue to taste it, which is undesirable, and it can convey to the consumer that not all of the actives are delivered to where they are needed.

In one example, the dosage form can be completely undetectable from the consumer's mouth once it is swallowed. The dosage forms as described herein can begin to dissolve once it is placed in the oral cavity and chewing begins, which can help reduce or eliminate toothpacking. In one example, the dosage form as described herein can have little detectable toothpacking after 2.5 minutes and no detectable toothpacking after 5 minutes.

The dosage forms of the present invention can provide little to no aftertaste. The dosage forms can have lower mouth coating than other antacid products. The dosage form as described herein can have little detectable mouth coating after 2.5 minutes and no detectable mouth coating after 5 minutes.

The dosage forms can provide long lasting relief from gastrointestinal symptoms. In one example the dosage form provides at least one hour of relief, in another example at least two hours, in another example at least four hours, in another example at least six hours, in another example at least eight hours, in another example at least ten hours, and in another example at least twelve hours.

The dosage form of the present invention can be any form. Non-limiting examples of forms can include tablets, granules, capsules, chewable tablets, and combinations thereof. In one example, the dosage form can be a chewable tablet that effervesces when chewed in the oral cavity. In one example, the dosage form is not an anti-caries agent, desensitizing agent, breath freshener, antibacterial, whitening agent or dentifrice. In one example the dosage form is not intended to be dissolved sub-lingually. In another example, the dosage form is not a gum and does not comprise gum base. In one example, the dosage form is not taken with water or dissolved in water. In one example, the dosage form is smooth when it dissolves, not gritty.

The dosage form can be any shape. Non-limiting examples of shapes can include round, oblong, oval, square, rectangular, diamond, triangular, five-sided, six-sided, seven-sided, eight-sided, irregular, or combinations thereof. In another example, the dosage form can be round. In one example, the dosage form is not shiny. In another example, the dosage form is matte.

The dosage form can be any size. In one example, the dosage form is a size that can easily fit inside the oral cavity. In one example the dosage form has a surface area from about 300 $mm^2$ to about 1300 $mm^2$, in another example from about 400 $mm^2$ to about 1000 $mm^2$, in another example from about 500 $mm^2$ to about 900 $mm^2$, in another example from about 600 $mm^2$ to about 800 $mm^2$, in another example from about 625 $mm^2$ to about 720 $mm^2$, and in another example from about 650 $mm^2$ to about 700 $mm^2$. In one example, the dosage form is circular or oval and the largest radius is from about 5 mm to about 30 mm, in another example from about 8 mm to about 25 mm, in another example about 10 mm to about 20 mm, and in another example about 13 mm to about 18 mm. In another example, the depth which is perpendicular from the radius, as measured from the highest point on the dosage form, is from about 2 mm to about 20 mm, in another example from about 3 mm to about 15 mm, in another example about 3.5 mm to about 10 mm, in another example about 4 mm to about 7 mm, and in another example about 4.5 mm to about 5.5 mm.

In another example, the dosage form is a chewable bi-layer tablet. In one example, each layer of the bi-layer tablet is a different color, but the tablets otherwise have the same formulations, for instance the first layer can be pink and the second layer can be white. In another example, one layer is effervescent and the other layer is not effervescent. In another example, one layer has a first active and another layer has a different second active. In another example, the bi-layer tablet comprises one layer that has a first flavor and another layer that has a second flavor.

Indicia can be debossed, embossed or printed on the dosage form. In one example, the indicia can be a brand mark. And in another example, the indicia can be a symbol that clearly indicates what the sensory experience is like for the dosage form, for example the indicia can be symbol that represents a bubble or bubbles.

The dosage form can be consumed one time per day or multiple times per day. The dosage forms can be consumed on a daily basis or only as needed when symptoms are present. In one example, the dosage form can be taken with a meal, snack, or beverage. In another example, the dosage form can be taken about 30 minutes, about 60 minutes, about 90 minutes, or about 120 minutes after eating. In another example, the dosage form can be taken on an empty stomach or without food. In another example, the dosage form can be taken without water.

In another example, the dosage form can be co-packaged or otherwise sold in combination with a medication intended to treat heartburn, such as omeprazole. The effervescent dosage form can provide immediate relief and the dosage form can be consumed on an as-needed basis as symptoms occur, while the heartburn medication provides extended relief and can be consumed at regular intervals.

In one example a consumer can ingest one chewable tablet per dose, in another example two chewable tablets per dose, in another example three chewable tablets per dose, and in another example four chewable tablets per dose. In one example, the consumer can consume at least one dose per day, in another example at least two doses per day, in another example at least three doses per day, and in another example at least four doses per day. In one example, the doses can be taken one to twelve times per day, in another example two to ten times per day, in another example four to six times a day, and in another example three to four times per day. In one example the doses can be taken on an as-needed basis when symptoms occur.

When the tablet dissolves in water to form a 1.0% by weight aqueous solution the pH can be measured using the pH Test Method described hereafter. In one example, the pH at equilibrium can be from about 6.0 to about 10, in another example from about 6.5 to about 9.5, in another example from about 7.0 to about 9.5, in another example from about 7.5 to about 9.0, in another example about 8.0 to about 8.9, and in another example about 8.25 to about 8.75, as determined by the pH Test Method. In one example, the pH at equilibrium can be about 8.5. In another example the pH at equilibrium can be greater than about 7.0, in another example greater than about 7.5, and in another example greater than about 8, as determined by the pH Test Method.

In one example, the pH after 2 minutes can be from about 3 to about 6, in another example from about 3 to about 5.5, in another example from about 4 to about 5.25, and in another example from about 4.5 to about 5, as determined by the pH Test Method. In one example, the pH after five minutes can be from about 4 to about 5.75, in another example from about 4.5 to about 5.5, and in another example from about 4.7 to about 5.2, as determined by the pH Test Method. In one example, the pH at 2 minutes and/or five minutes can be less than the pH at thirty seconds and/or at equilibrium.

Figures 2A, 2B:
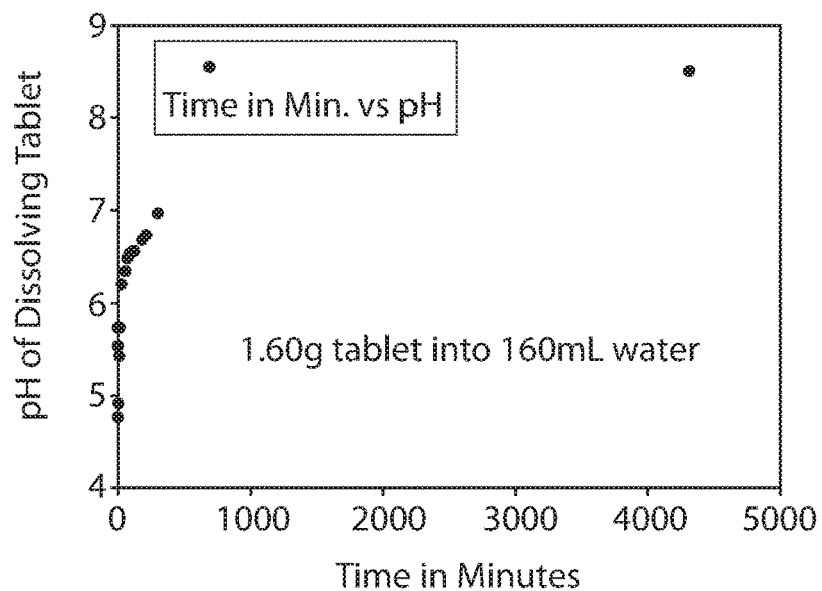
FIG. 2A is a pH Profile of Effervescent Chewable Tablet over 5000 Minutes.
FIG. 2B is a table that corresponds to the data points in FIG. 2A and shows the pH at specific times.

The pH over time of the composition in Example 1 can be seen in FIGS. 1 and 2. FIG. 1 shows the pH of the dissolving tablet from 0 to 35 minutes and FIGS. 2A and 2B show the pH of the dissolving tablet from 0 to 5000 minutes.

Consumers desire fast relief of their gastrointestinal symptoms, in particular heartburn. In one example, the acid can begin to neutralize when it contacts the pH neutralization agent, which can occur within minutes after consumption. In one example, heartburn relief can occur within about thirty minutes of ingesting the dose.

The effervescence can provide a unique sensory experience. In one example, the effervescence can help relieve pressure in the upper gastrointestinal track. This pressure relief can give the consumer some relief soon after consumption. In one example, the dosage form can cause the consumer to burp. In another example, the dosage form can cause the consumer to burp within three minutes.

In another example, the gas evolution of the dosage form can be greater than about 25 mL, in another example greater than about 25.5 mL, in another example greater than about 26 mL, in another example greater than about 26.5 mL, in another example greater than about 26.8 mL, and in another example greater than about 27 mL, as determined by the Gas Evolution Test Method described herein. In another example, the gas evolution can be from about 24 mL to about 32 mL, in another example about 24.5 mL to about 31 mL, in another example about 25 mL to about 30 mL, in another example about 26 mL to about 29.8 mL, and in another example about 27 mL to about 29.5 mL, as determined by the Gas Evolution Test Method described herein.

The dosage form can be taken as a calcium supplement and/or as an antacid to relieve heartburn, acid indigestion, and sour stomach.

The dosage form can comprise a pH neutralization agent. Non-limiting examples of pH neutralization agents can include alkali metal carbonates, hydroxides, and combinations thereof. Non-limiting examples of alkali metal carbonates can include calcium carbonate, magnesium carbonate, magnesium hydroxide, aluminum hydroxide, calcium hydroxide, and combinations thereof. In one example, the pH neutralization agent is not sodium carbonate because sodium carbonate is too soluble and therefore too much of it can react with the acid in the oral cavity which decreases the amount of pH neutralization agent that can neutralize stomach acid.

In one example, the pH neutralization agent is calcium carbonate. In one example, a dose contains 1000 mg of calcium carbonate, in another example 800 mg calcium carbonate, in another example 750 mg, in another example 600 mg, in another example 550 mg, in another example 500 mg, in another example 400 mg, and in another example 300 mg.

In one example the dosage forms can comprise from about 10% to about 75% calcium carbonate, in another example from about 18% to about 60%, in another example from about 22% to about 50%, in another example about 25% to about 40%, in another example about 26% to about 40%, in another example about 28% to about 34%, and in another example from about 29% to about 32%.

The calcium carbonate particles can be any size. If the particles are too large, the dosage form can have a gritty texture and the composition will dissolve slower. Dosage forms that are made with smaller particles can feel smoother in the consumer's oral cavity as well as dissolve faster than compositions that are made with larger particles. While not wishing to be bound by theory, it is believed that consumers do not perceive grittiness if the particles are no larger than about 300 μm. In one example, the particles can be no larger than about 750 μm in diameter prior to tableting, in another example no larger than about 600 μm, in another example no larger than about 500 μm, in another example no larger than about 400 μm, in another example no larger than about 350 μm, in another example no larger than about 325 μm, and in another example no larger than about 300 μm. In one example, from about 1% to about 50% of the calcium carbonate particles are less than 90 μm, in another example from about 10% to about 45%, in another example 25% to 42%, and in another example 30% to 40%.

In one example the dosage forms can comprise a gas reducer. Non-limiting examples of gas reducers can include simethicone, alpha galactosidase, charcoal tablets, and combinations thereof. In one example, the gas reducer can be simethicone. While not wishing to be bound by theory, the simethicone may help improve the sensory experience by making the dosage forms less gritty and making the composition less foamy. The simethicone can help alleviate gastrointestinal symptoms by relieving pressure and bloating associated with gas. In one example the dose contains from about 40 mg to about 250 mg of simethicone, in another example from about 50 mg to about 160 mg, in another example from about 60 mg to about 100 mg, and in another example from about 75 mg to about 85 mg. In one example the dosage forms can comprise from about 1% to about 11% simethicone, in another example about 2% to about 9%, in another example about 2.5% to about 7%, and in another example about 3% to about 6%. In another example the weight ratio of gas reducer to effervescent agent is greater than about 0.75:1, in another example greater than about 1:1, and in another example greater than about 1.15:1. In another example the weight ratio of gas reducer to effervescent agent is from about 0.5:2 to about 2.25:0.75, in another example from about 0.75:1.75 to about 2:1, in another example about 1:1 to about 1.5:1, in another example about 1.1:1 to about 1.4:1, in another example from about 1.15:1 to about 1.35:1, and in another example 1.2:1 to about 1.3:1.

Additional pharmaceutical actives can also be added to the dosage forms. Non-limiting examples of additional pharmaceutical actives can include alginic acid and alginate salts, aluminum hydroxide, famotidine, magnesium carbonate, magnesium hydroxide, magnesium trisilicate, loperamide, ranitidine, nizatidine, proton pump inhibitors, H2 antagonists, and combinations thereof. Non-limiting examples of proton pump inhibitors can include such as omeprazole, pantoprazole, lansoprazole, and combinations thereof. Non-limiting examples of H2 antagonists can include cimetidine, and combinations thereof. In one example, the composition can comprise from about 0.5% to about 50% additional pharmaceutical active, in another example from about 5% to about 40%, in another example from about 10% to about 35%, and in another example about 15% to about 30%. In one example, the dosage form comprises 10 mg of famotidine and 165 mg of magnesium hydroxide. In another example, the dosage form comprises 160 mg of aluminum hydroxide and 105 mg of magnesium carbonate. In another example, the dosage form comprises 80 mg of aluminum hydroxide and 14.2 mg of magnesium trisilicate. In one example, the dosage form does not contain alginic acid or alginate salts because these ingredients can lead to unfavorable organoleptic properties such as a gummy chew and/or stiff thick foam that is difficult to swallow.

The dosage forms can comprise an effervescent agent. In one example, the effervescent agent is an alkali metal bicarbonate. Non-limiting examples of alkali metal bicarbonates can include sodium bicarbonate, potassium bicarbonate, and combinations thereof. In one example, the dosage form comprises sodium bicarbonate. In one example the dosage form comprises from about 1% to about 20% effervescent agent, in another example about 2% to about 15%, in another example about 3% to about 10%, in another example about 4% to about 8%, and in another example about 5% to about 7%. If there is too much effervescent agent in the dosage form, the composition will taste bitter and there will be too much foam.

The effervescent agent can be more soluble in water than the pH neutralization agent. Since the effervescent agent can be more water soluble than the pH neutralization agent, the primary effervescent activity can come from the reaction of the acid and the effervescent agent and the majority of the pH neutralization agent cannot react in the oral cavity and is therefore able to neutralize acid in the stomach. In one example, less than 50% of the pH neutralization reacts with the acid in the oral cavity, in another example less than 40%, in another example less than 35%, in another example less than 25%, in another example less than 20%, in another example less than 15%, in another example less than 10%, and in another example less than 5%.

In one example the pH neutralization agent is at least 10-fold less water soluble than the effervescent agent, in another example at least 100-fold less soluble, and in another example at least 1000-fold less soluble. In another example the ratio of the water solubility of the effervescent agent to the pH neutralization agent is greater than 1000:1, in another example greater than 10,000:1, in another example greater than 40,000:1, in another example greater than 60,000:1, in another example greater than 70,000:1, in another example greater than 75,000:1, and in another example greater than 100,000:1.

The dosage forms can comprise an acid. The acid and the effervescent agent can react in the oral cavity to form carbon dioxide, giving the effervescence. The ratio of effervescent agent to acid can influence how much pH neutralization agent reacts in the oral cavity. In one example the molar ratio of effervescent agent to acid is from about 0.5:1 to about 6:1, in another example about 1:1 to about 5:1, in another example about 2:1 to about 4:1, and in another example about 2.5:1 to about 3.5:1. In one example, the weight ratio of effervescent agent to acid can be about 0.1:1 to about 1.5:1, in another example about 0.5:1 to about 1:1, and in another example about 0.7:1 to about 0.9:1.

In another example, the weight or molar ratio of the effervescent agent to the acid can be calculated from the reaction stoichiometry for the complete reaction to form carbon dioxide. While not wishing to be bound by theory, having the ratio of acid to effervescent agent approximately equal to the stoichiometric relationship for the generation of carbon dioxide protects the slower reacting pH neutralization reagent from being consumed in the reaction that produces the effervescence. In one example the ratio of effervescent agent to acid is from about 70% to about 130% of the stoichiometric relationship, in another example from about 80% to about 120%, in another example from about 90% to about 110%, and in another example the ratio of effervescent agent to acid is equal to the stoichiometric relationship.

Non-limiting examples of acid can include citric acid, tartaric acid, fumaric acid, malic acid, adipic acid, succinic acid, ascorbic acid, maleic acid, and combinations thereof. In the oral cavity, the acid reacts with the effervescent agent and gives off carbon dioxide, which produces the effervescent sensation. In one example, the dosage form can comprise citric acid. In one example, the dosage form does not comprise maleic acid. In one example the dosage form comprises from about 1% to about 15% acid, in another example about 2% to about 10%, in another example about 3% to about 8%, and in another example about 4% to about 6%. In one example, the chewable tablet can be 1600 mg and the can comprise greater than 3% acid because if the acid is less than 3% the consumer may think that there is too little effervescence. If the acid is too high the formulations can foam too much and have a sour taste.

In one example, the dosage form does not comprise a nutritive sweetener and comprises from about 5% to about 20% acid, in another example from about 6% to about 18% acid, and in another example from about 8% to about 15% acid.

The dosage form can comprise a lubricant. Non-limiting examples of lubricants can include sodium stearyl fumarate, magnesium stearate, calcium stearate, stearic acid, glyceryl behenate, and combinations thereof. In one example, the dosage form can comprise magnesium stearate. The lubricant can impact the hardness of the dosage form, for instance dosage forms that are made comprising 0.5% magnesium stearate can be harder than dosage forms that are made comprising 0.5% stearyl fumarate. In one example, the dosage form can comprise from about 0.05% to about 5% lubricant, in another example about 0.1% to about 3%, in another example about 0.25% to about 1.5%, in another example about 0.3% to about 1%, in another example about 0.35% to about 0.75%, and in another example about 0.4% to about 0.6%.

The dosage forms can also comprise a sweetener. The sweeteners can be natural or artificial. Non-limiting examples of sweeteners can include nutritive sweeteners, sugar alcohols, synthetic sweeteners, high intensity natural sweeteners, and combinations thereof. In one example, the dosage forms can comprise a nutritive sweetener and a synthetic sweetener. In one example, the dosage forms can comprise from about 0.05% to about 70% sweetener, in another example from about 0.1% to about 60%, in another example from about 1% to about 50%, in another example about 5% to about 45%.

Non-limiting examples of nutritive sweeteners can include sucrose, dextrose, glucose, fructose, lactose, tagatose, maltose, trehalose, and combinations thereof. In one example, the dosage forms can comprise sucrose. In one example the dosage form can comprise from about 10% to about 70% nutritive sweetener, in another example from about 20% to about 60%, in another example about 30% to about 55%, in another example about 35% to about 50%, in another example about 40% to about 48%, and in another example about 42% to about 47%.

In one example, the dosage form may not comprise a nutritive sweetener. In one example, the sweetener can comprises a sweetener selected from the group comprising sugar alcohols, synthetic sweeteners, high intensity natural sweeteners, and combinations thereof. The dosage forms can be sold as reduced sugar, lower in sugar, low in sugar, or sugar free.

Non-limiting examples of sugar alcohols can include xylitol, sorbitol, mannitol, maltitol, lactitol, isomalt, erythritol, and combinations thereof. In one example the dosage form can comprise from about 10% to about 70% sugar alcohol, in another example from about 20% to about 60%, in another example about 30% to about 55%, in another example about 35% to about 50%, in another example about 40% to about 48%, and in another example about 42% to about 47%.

Non-limiting examples of synthetic sweeteners can include aspartame, acesulfame potassium, alitame, sodium saccharin, sucralose, neotame, cyclamate, and combinations thereof. In one example, the dosage forms comprise sucralose. In another example the dosage forms can comprise both sucralose and sucrose. In one example the dosage form can comprise from about 0.01% to about 10% artificial sweetener, in another example from about 0.05% to about 5%, in another example from about 0.08% to about 3%, and in another example from about 0.09% to about 1%, in another example from about 0.1% to about 0.5%, and in another example about 0.2% to about 0.25%.

Non-limiting examples of high intensity natural sweeteners can include neohesperidin dihydrochalcone, stevioside, rebaudioside A, rebaudioside C, dulcoside, monoammonium glycrrhizinate, thaumatin, and combinations thereof. In one example the dosage form can comprise from about 0.01% to about 10% high intensity natural sweeteners, in another example from about 0.05% to about 5%, in another example from about 0.08% to about 3%, in another example from about 0.09% to about 1%, in another example from about 0.1% to about 0.5%, and in another example about 0.2% to about 0.25%.

The dosage forms can also include a flavor. Non-limiting examples of flavors that can include natural flavoring agents, artificial flavoring agents, artificial extracts, natural extracts and combination thereof. Non-limiting examples of flavors can include vanilla, honey, lemon, lemon honey, cherry vanilla, peach, honey ginger, chamomile, cherry, cherry cream, mint, vanilla mint, dark berry, black berry, raspberry, peppermint, spearmint, honey peach, acai berry, cranberry, honey cranberry, tropical fruit, dragon fruit, wolf berry, red stem mint, pomegranate, black current, strawberry, lemon, lime, peach ginger, orange, orange cream, cream sickle, apricot, anethole, ginger, jack fruit, star fruit, blueberry, fruit punch, lemon grass, chamomile lemon grass, lavender, banana, strawberry banana, grape, blue raspberry, lemon lime, coffee, espresso, cappuccino, honey, wintergreen mint, bubble gum, tart honey lemon, sour lemon, sour cherry, green apple, boysenberry, rhubarb, strawberry rhubarb, persimmon, green tea, black tea, red tea, white tea, honey lime, cherry lime, apple, tangerine, grapefruit, kiwi, pear, vanillin, ethyl vanillin, maltol, ethyl-maltol, pumpkin, carrot cake, white chocolate raspberry, chocolate, white chocolate, milk chocolate, dark chocolate, chocolate marshmallow, apple pie, cinnamon, hazelnut, almond, cream, crème brûlée, caramel, caramel nut, butter, butter toffee, caramel toffee, aloe vera, whiskey, rum, cocoa, licorice, pineapple, guava, melon, watermelon, elder berry, oral cavity cooler, raspberries and cream, peach mango, tropical, cool berry, lemon ice, nectar, spicy nectar, tropical mango, apple butter, peanut butter, tangerine, tangerine lime, marshmallow, cotton candy, apple cider, orange chocolate, citral, denatonium benzoate, ethyl maltol, malic acid, menthol, and combinations thereof.

In one example, the dosage form can comprise from about 0.05% to about 10% flavor, in another example from about 0.1% to about 8%, in another example from about 0.3% to about 6%, in another example from about 0.5% to about 3%, in another example about 0.6% to about 1.5%, in another example about 0.7% to about 1%, and in another example about 0.8% to about 0.9%.

The dosage form can comprise a colorant. Non-limiting examples of colorants can include FD&C blue #1, FD&C blue #2, D&C blue #4, D&C blue #9, FD&C green #3, D&C green #5, D&C green #6, D&C green #8, D&C orange #4, D&C orange #5, D&C orange #10, D&C orange #11, FD&C red #3, FD&C red #4, D&C red #6, D&C red #7, D&C red #17, D&C red #21, D&C red #22, D&C red #27, D&C red #28, D&C red #30, D&C red #31, D&C red #33, D&C red #34, D&C red #36, D&C red #39, FD&C red #40, D&C violet #2, FD&C yellow #5, FD&C yellow #6, D&C yellow #7, Ext. D&C yellow #7, D&C yellow #8, D&C yellow #10, D&C yellow #11, and combinations thereof.

In one example, the dosage form can comprise from about 0.01% to about 1% colorant, in another example about 0.05% to about 0.75%, in another example about 0.1% to about 0.5%, and in another example about 0.15% to about 0.25%.

The dosage forms can include sensates. Non-limiting examples of sensates can include cooling sensates, warming sensates, tingling sensates, and combinations thereof. Sensates can be useful to deliver signals to the consumer. In one example, the dosage form can comprise a cooling sensate. It is believed that cooling sensates can help consumers with digestive problems, in particular heartburn, feel that they are getting immediate relief.

In one example, the dosage form can comprise from about 0.005% to about 5% sensate, in another example from about 0.05% to about 3%, in another example from about 0.01% to about 1%, and in another example about 0.1% to about 0.5%.

Non-limiting examples of cooling sensates can include WS-23 (2-Isopropyl-N,2,3-trimethylbutyramide), WS-3 (N-Ethyl-p-menthane-3-carboxamide), WS-30 (1-glyceryl-p-mentane-3-carboxylate), WS-4 (ethyleneglycol-p-methane-3-carboxylate), WS-14 (N-t-butyl-p-menthane-3-carboxamide), WS-12 (N-(4-,ethoxyphenyl)-p-menthane-3-carboxamide), WS-5 (Ethyl-3-(p-menthane-3-carboxamido) acetate, Menthone glycerol ketal (sold as Frescolat® MGA by Haarmann & Reimer), (−)-Menthyl lactate (sold as Frescolat® ML by Haarmann & Reimer), (−)-Menthoxypropane-1,2-diol (sold as Coolant Agent 10 by Takasago International), 3-(1-menthoxy)propane-1,2-diol, 3-(1-Menthoxy)-2-methylpropane-1,2-diol, (−)-Isopulegol is sold under the name "Coolact P®" by Takasago International., cis & trans p-Menthane-3,8-diols(PMD38)—Takasago International, Questice® (menthyl pyrrolidone carboxylate), (1R,3R,4S)-3-menthyl-3,6-dioxaheptanoate—Firmenich, (1R,2S,5R)-3-menthyl methoxyacetate—Firmenich, (1R,2S,5R)-3-menthyl 3,6,9-trioxadecanoate—Firmenich, (1R,2S,5R)-menthyl 11-hydroxy-3,6,9-trioxaundecanoate—Firmenich, (1R,2S,5R)-3-menthyl (2-hydroxyethoxy)acetate—Firmenich, Cubebol—Firmenich, Icilin also known as AG-3-5, chemical name 1-[2-hydroxyphenyl]-4-[2-nitrophenyl-]1-1,2,3,6-tetrahydropyrimidine-2-one), 4-methyl-3-(1-pyrrolidinyl)-2[5H]-furanone, Frescolat ML—menthyl lactate, Frescolat MGA—menthone glycerin acetal, Peppermint oil, Givaudan 180, L-Monomenthyl succinate, L-monomenthyl glutarate, 3-1-menthoxypropane-1,2-diol—(Coolact 10), 2-1-menthoxyethanol (Cooltact 5), TK10 Coolact (3-1-Menthoxy propane-1,2-diol), Evercool 180 (N-p-benzeneacetonitrile-menthane carboxamide), menthol, spearmint and combinations thereof.

Non-limiting examples of warming sensates can include TK 1000, TK 1 MM, Heatenol—Sensient Flavors, Optaheat—Symrise Flavors, Cinnamon, Polyethylene glycol, Capsicum, Capsaicin, Curry, FSI Flavors, Isobutavan, Ethanol, Glycerin, Nonivamide 60162807, Hotact VEE, Hotact 1 MM, piperine, optaheat 295 832, optaheat 204 656, optaheat 200 349, and combinations thereof.

Non-limiting examples of tingling sensates can include sichuan pepper, hydroxy alpha sanshool, Jambu extracts, spilanthol, and combinations thereof.

The dosage forms can be packaged in any suitable package. Effervescent dosage forms can be moisture sensitive and can require packaging that provides a moisture barrier. The dosage forms can be packaged in blister packaging, laminated foil or plastic sachet, or a bottle. In one example, the dosage forms can be packaged in single doses so they are easily portable and can be carried in a purse, pocket, or brief case. In another example, the packaging can be substantially rigid which can prevent the dosage form from being crushed. In one example, the packaging can be child resistant. In one example, the packaging can be clear. In one example the package can include a desiccant.

Gas Evolution Test

Different formulas were tested to assess the amount of gas ($CO_2$) that evolved from the tablet or blend when exposed to water, which initiated the acid-base reaction that causes the effervescent attribute.

First, tablets A, B, and C were made according to the procedure described in the examples hereafter. Tablet B has 10% less citric acid than Tablet A and Tablet C has 10% more citric acid than Tablet A.

|  | Trial | Volume Gas (mL) |
|---|---|---|
| Tablet A | 1 | 26.5 |
|  | 2 | 26.5 |
|  | 3 | 28.0 |
|  | Mean | 27.0 |
| Tablet B | 1 | 25.0 |
|  | 2 | 23.5 |
|  | 3 | 24.5 |
|  | Mean | 24.3 |
| Tablet C | 1 | 29.5 |
|  | 2 | 30.0 |
|  | 3 | 29.5 |
|  | Mean | 29.7 |

Tablet C, which had the most citric acid, had the highest volume of gas and Tablet B, which had the least amount of citric acid, had the lowest volume of gas.

Effervescence Test

The Gas Evolution Test showed that the more citric acid present in the tablet, the more $CO_2$ the tablet would produce. However, it was still necessary to determine the ideal amount of effervescence while still optimizing other organoleptic properties such as taste, tablet hardness, and the residue left in the mouth after consumption. Testing was

|  | Tablet A | | Tablet B | | Tablet C | |
|---|---|---|---|---|---|---|
|  | wt % | mg/tablet | wt % | mg/tablet | wt % | mg/tablet |
| Calcium Carbonate | 34.37 | 550 | 34.37 | 550 | 34.37 | 550 |
| Simethicone | 7.69 | 123 | 7.69 | 123 | 7.69 | 123 |
| Sucrose | 45.24 | 723.6 | 45.74 | 731.8 | 44.74 | 715.8 |
| Sucralose | 0.10 | 1.6 | 0.10 | 1.6 | 0.1 | 1.6 |
| Citric Acid | 5.00 | 80 | 4.50 | 72 | 5.50 | 88 |
| Sodium Bicarbonate | 6.25 | 100 | 6.25 | 100 | 6.25 | 100 |
| Flavor, Cherry | 0.85 | 13.6 | 0.85 | 13.6 | 0.85 | 13.6 |
| Sodium Stearyl Fumarate | 0.5 | 8 | 0.5 | 8 | 0.5 | 8 |
| Total | 100 | 1600 | 100 | 1600 | 100 | 1600 |

Then, the Gas Evolution Test Method was performed to determine the amount of gas ($CO_2$) that evolved from Tablets A, B, and C. Each tablet weighed approximately 1600 mg.

performed on five panelists over a period of about two weeks. Each panelist chewed and then ingested six formulations that had different balanced amounts of citric acid and sodium bicarbonate and/or flavor.

Panelists ingested the six formulations below.

|  | Tablet #1 Cherry Flavor, Low Level Citric Acid | | Tablet #2 Cherry Flavor, Med. Level Citric Acid | | Tablet #3 Cherry Flavor, High Level Citric Acid | |
| --- | --- | --- | --- | --- | --- | --- |
|  | wt % | g/batch | wt % | g/batch | wt % | g/batch |
| Calcium Carbonate | 27.48 | 5.5 | 27.50 | 5.5 | 27.50 | 5.5 |
| Simethicone | 5.05 | 1.01 | 5.00 | 1.00 | 5.00 | 1.00 |
| Sucrose | 59.36 | 11.88 | 54.97 | 10.99 | 50.54 | 10.11 |
| Sucralose | 0.11 | 0.022 | 0.11 | 0.021 | 0.11 | 0.022 |
| Citric Acid | 2.9 | 0.58 | 4.83 | 1.0 | 6.75 | 1.35 |
| Sodium Bicarbonate | 3.75 | 0.75 | 6.25 | 1.25 | 8.75 | 1.75 |
| Flavor, Cherry | 0.85 | 0.17 | 0.85 | 0.17 | 0.85 | 0.17 |
| Sodium Stearyl Fumarate | 0.5 | 0.10 | 0.5 | 0.10 | 0.5 | 0.10 |
| Total | 100 | 20.012 | 100 | 20.001 | 100 | 20.002 |

|  | Tablet #4 Lemon Flavor, Low Level Citric Acid | | Tablet #5 Lemon Flavor, Med. Level Citric Acid | | Tablet #6 Lemon Flavor, High Level Citric Acid | |
| --- | --- | --- | --- | --- | --- | --- |
|  | wt % | g/batch | wt % | g/batch | wt % | g/batch |
| Calcium Carbonate | 27.20 | 5.5 | 27.50 | 5.5 | 27.50 | 5.5 |
| Simethicone | 5.09 | 1.03 | 5.13 | 1.04 | 4.95 | 1.00 |
| Sucrose | 59.38 | 12.01 | 54.32 | 11.02 | 50.70 | 10.25 |
| Sucralose | 0.11 | 0.022 | 0.99 | 0.2 | 0.11 | 0.023 |
| Citric Acid | 2.87 | 0.58 | 4.77 | 0.97 | 6.68 | 1.35 |
| Sodium Bicarbonate | 3.72 | 0.75 | 6.16 | 1.25 | 8.67 | 1.75 |
| Flavor, Lemon | 1.04 | 0.21 | 1.08 | 0.22 | 1.05 | 0.21 |
| Sodium Stearyl Fumarate | 0.59 | 0.12 | 0.54 | 0.11 | 0.54 | 0.11 |
| Total | 100 | 20.224 | 100 | 20.286 | 100 | 20.218 |

The five panelists graded each tablet in terms of how much of each sensory attribute he or she noticed in each tablet. The grades were as follows: much too much (+2), a little too much (+1), ideal (0), a little too much (−1), and much too little (−2).

Below are the results from the test and the numbers indicate the mean score from the five panelists who graded each tablet.

| Sensory Attribute | Mean Score by Tablet Number | | | | | |
| --- | --- | --- | --- | --- | --- | --- |
|  | #1 | #2 | #3 | #4 | #5 | #6 |
| Flavor Intensity | 0.4 | 0.2 | 0.2 | 0.0 | 0.4 | 0.6 |
| Fizzing Sensation | −1.2 | −0.2 | 0.6 | −0.75 | 0.4 | −0.2 |
| Foaming Sensation | −0.2 | 0.2 | 0.4 | 0.25 | 0.2 | 0.3 |
| Popping Sensation | −0.6 | 0.2 | 0.2 | −0.25 | 0.0 | −0.4 |
| Sweetness | 0.4 | 0.2 | 0.2 | 0.25 | 0.2 | 0.2 |
| Saltiness | −0.2 | 0.0 | 0.2 | 0.0 | 0.2 | 0.2 |
| Sourness | 0.2 | 0.4 | 0.6 | 0.25 | 0.6 | 1.0 |
| Bitterness | 0.4 | 0.0 | 0.0 | 0.0 | 0.6 | 0.2 |
| Aftertaste | 0.4 | 0.2 | 0.2 | 0.25 | 0.6 | 0.2 |
| Tablet Hardness | −0.2 | 0.0 | 0.0 | 0.25 | 0.6 | 0.2 |
| Residue left in mouth | 0.4 | 0.2 | 0.0 | 0.25 | 0.0 | 0.0 |

The panelists had a preference towards the cherry flavor and thought that the lemon flavor in combination with a citric acid concentration that provided the preferred amount of fizzing was too sour. With the cherry flavoring, Tablet #2 had a mean fizzing score of −0.2, which is a little too little, and Formulation #3 had a mean fizzing score of 0.6, which is a little too much. Therefore, it was determined that 5% citric acid could provide a good mouth feel, that does not foam too much, and is not overly sour.

Sensation Grading

Consumer studies were performed to understand the preferred sensory attributes for effervescence which includes the level of the effervescence sensation, the quality or type of sensation (i.e. foam, fizz, pop), and the desired flavor characteristics.

Panelists were selected using the following criteria:
60% of the participants were women and 40% were men
All participants had to be over the age of 18
No past 6 month participation in Digestive Wellness research
No known allergies to any foods, flavors, colorants, preservatives, calcium carbonate, simethicone, sucrose, citric acid, sodium bicarbonate, sucralose, sodium stearyl fumarate, mannitol, fructose, sorbitol, corspovidone, polyvinyl acetate
All are the primary decision maker for their health related issues
All suffer from heartburn and or gas/fullness at least one time per week
All are effervescent users or open to using effervescent products such as Alka Seltzer®, Gaviscon®, Eno®, or Picot® Sal de Uvas Panelists sampled eight products and gave their reactions by writing down their thoughts independently before sharing with the group. The panelists also graded each product in terms of ideal amount of sensation. The grades were as follows: much too much (+2), a little too much (+1), ideal (0), a little too little (−1), and much too little (−2). For the products which are not swallowed (e.g., soap), the moderator directed the panelists to imagine what this might feel like in their mouth.

Prior to testing each product, the panelists consumed a cracker, either a Ritz® Cracker or a saltine, and water to cleanse the palate. One at a time the products were handed to the panelists to test. The food/beverage products were chewed (if solid) and then ingested. Panelists had the option to expectorate the product, if desired. However, all of the panelists swallowed the products. After sampling the product, the panelists marked their reactions on the worksheets. Then, the panelists and the moderator discussed their experience (washout period) before moving onto the next product.

The panelists sampled the following products, in the order listed below, and the moderator gave the panelists the usage instructions before sampling each product.

| Product | Usage Instruction |
|---|---|
| 1 Zotz ® Orange Candy<br>Manufactured by Andre Prost, Inc.<br>Purchased May 5, 2011 from Amazon.com | Each panelist gets 1 candy (use same flavor for all participants in the group). Chew and swallow (or expectorate if desired) |
| 2 Pellegrino ® Sparkling Water<br>Manufactured by San Pellegrino S.P.A.<br>Lot #: PRD Dec. 16, 2010 and PRD Jan. 27, 2011<br>Purchased Jun. 8, 2011 from Meijer ®,<br>Loveland Ohio | Pour a serving into paper cup. Drink and swallow (or expectorate if desired<br>Allow to dissolve in mouth and swallow (or expectorate if desired) |
| 3 Pop Rocks ® Strawberry Candy<br>Manufactured by Zeta Espacial SA<br>Lot # SBB11-2013 257 34 22110<br>Purchased Jun. 8, 2011 from Supreme Nut & Candy, Cincinnati, Ohio | Allow to dissolve in mouth and swallow (or expectorate if desired) |
| 4 Foaming Hand Soap<br>Purchased Jun. 8, 2011 from Meijer ®,<br>Loveland Ohio | Dispense into a clear plastic cup and pass around for visual look. The panelists are instructed to imagine what this might feel like in their mouths. |
| 5 Skittles ® Fizzl'd Fruits<br>Manufactured by Wm. Wrigley Jr. Company<br>Purchased May 17, 2011 from Amazon.com | Panelists must share a bag with one other person. Chew and swallow (or expectorate if desired) |
| 6 Scope ® Whitening Mouthwash<br>Manufactured by Procter & Gamble<br>Lot # L10065395UB<br>Purchased Jun. 8, 2011 from Meijer ®,<br>Loveland, Ohio | Measure 15 mL using lid then pour into paper cup. Hold in mouth then expectorate. Do not swallow. |
| 7 A&W ® Root Beer<br>Canned by American Bottling Company under the authority of Dr. Pepper/Seven Up<br>Lot # F1152LU4B43 and F1152LU41342<br>Purchased Jun. 8, 2011 from Meijer ®,<br>Loveland, Ohio | Drink directly from can and swallow (or expectorate if desired) |
| 8 Kellogg's ® Rice Krispies ® Cereal<br>Manufactured by Kellogg's<br>Lot # KBC 0134 06 10<br>Purchased Jun. 8, 2011 from Meijer ®,<br>Loveland Ohio | Pour a serving into a paper cup. Chew and swallow (or expectorate if desired) |

Below are the results from the consumer tests and the numbers indicate the number of panelists who gave the grade to each product.

|  | Much Too Much | A Little Too Much | Ideal | A Little Too Little | Much too Little |
|---|---|---|---|---|---|
| Zotz ® Orange Candy | 10 | 1 |  | 1 |  |
| Pellegrino ® Sparkling Water | 1 | 1 | 1 | 4 | 5 |
| Pop Rocks ® Strawberry Candy | 3 | 6 | 2 | 1 |  |
| Foaming Hand Soap | 3 | 3 |  | 4 | 2 |
| Skittles ® Fizzl'd Fruits |  | 2 | 2 | 7 | 1 |
| Scope ® Whitening Mouthwash | 1 | 5 | 2 | 2 | 2 |
| A&W ® Root Beer | 1 | 2 | 6 | 3 |  |
| Kellogg's ® Rice Krispies ® Cereal |  | 1 | 4 | 2 | 5 |

Based on the products tested, the A&W® Root Beer had the overall sensory experience that was graded ideal by six of the panelists. Qualitatively, the consumers believed that A&W® Root Beer had constant fizzing with no bad aftertaste or film and the liquid was easy to swallow. The majority of panelists thought that Zotz® Orange Candy and Pop Rocks® provided much too much or a little too much sensory experience and consumers described the experience with these products as "violent". While the majority of consumers thought that Pellegrino® Sparkling Water provided too little sensory experience.

Gas Evolution Test Method

First, the apparatus is assembled. A plastic cryo-vial, approximately 2 mL in total capacity, is filled with approximately 1.75 mL water, and set aside. The reaction flask, a 125 mL Erlenmeyer flask with a 24/40 ground glass jointed top, is connected to silicone tubing using a ground glass jointed stopper with a hose fitting. The tubing is connected to the aspirator end of a plastic 50 mL serological pipette with the tip end removed. The pipette is dropped into a cylinder of water and water is added q.s. until it reaches the 0 mark of the pipette.

Next, the dosage form is analyzed. The sample weight is recorded. Approximately 1.6 grams of sample is used. The tablet is ground using a mortar and pestle to a powder. The powder is transferred to the reaction flask. The cryo-vial with 1.75 mL water is placed upright into the reaction flask. The tubing is connected, which closes the system. The vial is tipped over and the mixture is agitated by rocking and swirling the reaction flask. On initial mixing, the solid-water mass looks unwetted. After a few seconds gas is observed to evolve and the mixture becomes foamy/bubbly. The contents are continually mixed. After approximately 1.5 minutes, the foam breaks to a wetted solid mixture. Mixing is continued for approximately 3 minutes (total) at which time gas evolution has ceased. The pipette is raised to align the two meniscuses and the volume of water displaced is recorded.

The gas constant equation: Vol=nRT/P is used to calculate the volume of gas where n=moles
R=constant value of 8.314
T=Temp ° K (ambient=300° K)
P=Pressure kPa (760 mmHg=100 kPa)

The volume (mL) is determined by repeating the Gas Evolution Test three times and calculating the mean volume.

pH Test Method

First, calibrate the Thermo Scientific Orion 320 pH meter. Do this by turning on the pH meter and waiting for 30 seconds. Then take the electrode out of the storage solution, rinse the electrode with distilled water, and carefully wipe the electrode with a scientific cleaning wipe, such as a Kimwipe®. Submerse the electrode in the pH 7 buffer and press the calibrate button. Wait until the pH icon stops flashing and press the calibrate button a second time. Rinse the electrode with distilled water and carefully wipe the electrode with a scientific cleaning wipe. Then submerse the electrode into the pH 4 buffer and wait until the pH icon stops flashing and press the measure button. Rinse the electrode with distilled water and carefully wipe with a scientific cleaning wipe. Now the pH meter is calibrated and can be used to test the pH of a solution.

Make a 1% solution of the entire effervescent dosage form. In one example, a 1.60 gram tablet is placed into a 160 mL of distilled water to form a 1% solution. The tablet is not crushed and the water is 23° C. The solution is not stirred at any time. The pH is measured at certain intervals using the calibrated pH meter. After three days, the pH at equilibrium can be measured.

All exemplified amounts are concentrations by weight of the total composition, i.e., wt/wt percentages, unless otherwise specified.

The following compositions can be prepared in accordance with the present invention:

|  | Example 1 | | Example 2 | |
| --- | --- | --- | --- | --- |
|  | wt % | mg/tablet | wt % | mg/tablet |
| Calcium Carbonate[1] | 34.37 | 550 | 34.37 | 550 |
| Simethicone[2] | 7.69 | 123 | 7.69 | 123 |
| Sucrose | 45.24 | 723.80 | 45.04 | 720.60 |
| Sucralose | 0.10 | 1.6 | 0.1 | 1.6 |
| Citric Acid | 5.00 | 80 | 5.00 | 80 |
| Sodium Bicarbonate | 6.25 | 100 | 6.25 | 100 |
| flavor, Cherry | 0.85 | 13.6 | 0.85 | 13.6 |
| FD&C Red #40 Aluminum Lake | 0 | 0 | 0.2 | 3.2 |
| Magnesium Stearate | 0.50 | 8 | 0.50 | 8 |
| Total | 100 | 1600 | 100 | 1600 |

[1]Barcroft™ CS90, directly compressible calcium carbonate comprises 90% calcium carbonate and 10% starch, available from SPI Pharma™ (Lewes, Delaware)
[2]Barcroft™ SIM DC100, simethicone powder assay, % (as simethicone) 60-70%, available from SPI Pharma™ (Lewes, Delaware)

|  | Example 3 | | Example 4 | | Example 5 | |
| --- | --- | --- | --- | --- | --- | --- |
|  | wt % | mg/tablet | wt % | mg/tablet | wt % | mg/tablet |
| Calcium Carbonate[3] | 34.37 | 550 | 34.37 | 550 | 34.37 | 550 |
| Simethicone[4] | 7.69 | 123 | 7.69 | 123 | 7.69 | 123 |
| Sucrose | 45.10 | 721.40 | 0 | 0 | 0 | 0 |
| Xylitol | 0 | 0 | 45.24 | 723.80 | 0 | 0 |
| Erythritol | 0 | 0 | 0 | 0 | 45.24 | 723.80 |
| Sucralose | 0.1 | 1.6 | 0.1 | 1.6 | 0.1 | 1.6 |
| Citric Acid | 5.00 | 80 | 5.00 | 80 | 5.00 | 80 |
| Sodium Bicarbonate | 6.25 | 100 | 6.25 | 100 | 6.25 | 100 |
| Flavor, Cherry | 0 | 0 | 0.85 | 13.6 | 0.85 | 13.6 |
| Flavor, Lemon | 1 | 16 | 0 | 0 | 0 | 0 |
| Magnesium Stearate | 0 | 0 | 0.5 | 8 | 0 | 0 |
| Sodium Stearyl Fumarate | 0.5 | 8 | 0 | 0 | 0 | 0 |
| Total | 100 | 1600 | 100 | 1600 | 100 | 1592 |

[3]Barcroft™ CS90, directly compressible calcium carbonate comprises 90% calcium carbonate and 10% starch, available from SPI Pharma™ (Lewes, Delaware)
[4]Barcroft™ SIM DC100, simethicone powder assay, % (as simethicone) 60-70%, available from SPI Pharma™ (Lewes, Delaware)

EXAMPLES

The following example further describes and demonstrates embodiments within the scope of the present invention. The examples are given solely for the purpose of illustration and are not to be construed as limitations of the present invention, as many variations thereof are possible without departing from the spirit and scope of the invention.

Examples 1 through 5 were made according to the following procedure. The sweeteners, calcium carbonate, simethicone powder, citric acid, bicarbonate, and flavors were deagglomerated and passed through a number 20 screen into a one cubic foot blender. The ingredients were mixed for five minutes. Then, the lubricant was deagglomerated and passed through a number 20 screen into the one cubic foot blender. All of the ingredients were mixed for two additional minutes to form the final ingredient blend. The final ingredient blend was discharged from the mixer and put in lined five gallon bucket.

Then, the final ingredient blend was put into the tablet machine hopper. The tablet machine was started, while the operator controlled the paddle speed and fill cams in order to control the size of the tablets. Then the operator focused on the pre-compression forces (0-2 kN), compression forces (5-25 kN), and injection forces (50-800 N) and optimized the tablet hardness (3-14 kp), then tablet thickness (5.0-7.0 mm). After all of the parameters were optimized, the final ingredient blend was compressed to form the final tablets.

After the final tablets were formed, they were collected and then inspected to ensure they products met the specifications, such as hardness and thickness, and then the final tablets were placed in the final packaging.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An effervescent chewable dosage form comprising:
   a. from about 28% to about 34% of a pH neutralization agent; wherein the pH neutralization agent is calcium carbonate;
   b. from about 4% to about 6% of citric acid;
   c. from about 5% to about 7% of an effervescent agent; wherein the effervescent agent is sodium bicarbonate;
   d. from about 2% to about 9% of a gas reducer; wherein the gas reducer is simethicone and;
   e. from about 35% to about 50% of a nutritive sweetener; wherein the effervescent chewable dosage form is a tablet.

2. The effervescent chewable dosage form of claim 1 further comprising a synthetic sweetener.

3. The effervescent chewable dosage form of claim 2 wherein the synthetic sweetener is sucralose.

4. The effervescent chewable dosage form of claim 1 further comprising from about 0.05% to about 5% sucralose.

5. The effervescent chewable dosage form of claim 1 wherein the dosage form has a gas evolution of from about 24 mL to 32 mL.

6. The effervescent chewable dosage form of claim 1 further comprising starch.

7. The effervescent chewable dosage form of claim 6 comprising about 3.47% starch.

8. The effervescent chewable dosage form of claim 1 further comprising a lubricant.

9. The effervescent chewable dosage form of claim 1 wherein the tablet comprises a tablet breaking force of about 4 kp to about 8.5 kp.

10. The effervescent chewable dosage form of claim 1 wherein the ratio of the effervescent agent to the citric acid is from 80% to 120% of the stoichiometric relationship.

11. A dose of an effervescent chewable dosage form comprising:
    a. from about 300 mg to about 600 mg calcium carbonate;
    b. about 100 mg sodium bicarbonate;
    c. from about 72 mg to about 88 mg of an acid; wherein the acid is citric acid;
    d. from about 50 mg to about 160 mg of a gas reducer, wherein the gas reducer is simethicone; and
    e. from about 720.60 mg to about 723.80 mg of a nutritive sweetener;
    wherein the effervescent chewable dosage form is a tablet.

12. The effervescent chewable dosage form of claim 11 comprising about 495 mg calcium carbonate, about 123 mg simethicone, and about 80 mg citric acid.

13. The effervescent chewable dosage form of claim 11 wherein the gas evolution of the dosage form is greater than about 25 mL.

14. The effervescent chewable dosage form of claim 11 further comprising a synthetic sweetener.

15. The effervescent chewable dosage form of claim 11 wherein the synthetic sweetener is sucralose.

* * * * *